United States Patent
Gerrans et al.

(10) Patent No.: US 8,597,239 B2
(45) Date of Patent: Dec. 3, 2013

(54) ABRADING BALLOON CATHETER FOR EXTRAVASATED DRUG DELIVERY

(75) Inventors: Lawrence J. Gerrans, San Anselmo, CA (US); Erhan H. Gunday, Great Neck, NY (US)

(73) Assignee: Sanovas, Inc., Sausalito, CA (US)

( * ) Notice: Subject to any disclaimer, the term of this patent is extended or adjusted under 35 U.S.C. 154(b) by 0 days.

(21) Appl. No.: 13/037,826

(22) Filed: Mar. 1, 2011

(65) Prior Publication Data

US 2011/0152683 A1     Jun. 23, 2011

Related U.S. Application Data

(63) Continuation-in-part of application No. 12/269,495, filed on Nov. 12, 2008, now Pat. No. 8,226,601.

(51) Int. Cl.
*A61M 29/00* (2006.01)

(52) U.S. Cl.
USPC ....................................... 604/96.01

(58) Field of Classification Search
USPC ....................................... 604/96.01
See application file for complete search history.

(56) References Cited

U.S. PATENT DOCUMENTS

| | | | |
|---|---|---|---|
| 3,720,199 A * | 3/1973 | Rishton et al. | 600/18 |
| 4,186,745 A | 2/1980 | Lewis et al. | |
| 4,423,725 A | 1/1984 | Baran et al. | |
| 4,446,867 A | 5/1984 | Leveen et al. | |
| 4,636,195 A | 1/1987 | Wolinsky | |
| 4,773,899 A | 9/1988 | Spears | |
| 4,824,436 A * | 4/1989 | Wolinsky | 604/509 |
| 4,921,484 A | 5/1990 | Hillstead | |
| 4,994,033 A | 2/1991 | Shockey et al. | |
| 5,049,132 A | 9/1991 | Shaffer et al. | |
| 5,100,425 A | 3/1992 | Fischell et al. | |
| 5,196,017 A | 3/1993 | Silva et al. | |

(Continued)

FOREIGN PATENT DOCUMENTS

| | | |
|---|---|---|
| EP | 0894507 A2 | 2/1999 |
| EP | 1913882 A1 | 4/2008 |

(Continued)

OTHER PUBLICATIONS

Altinoz et al., "Noscapine and diltiazem augment taxol and radiation-induced S-phase arrest and clonogenic death of C6 glioma in vitro", May 2006, Surgical Neurology, 65(5):478-84.*

(Continued)

*Primary Examiner* — Jason Flick
(74) *Attorney, Agent, or Firm* — St. Onge Steward Johnston & Reens LLC

(57) ABSTRACT

A method of extravasated drug delivery is disclosed, including inserting a catheter with a first balloon, a second balloon, and a third balloon positioned between the first and second balloons and having a wall with an abrasive outer surface, into a bodily cavity, inflating the first and second balloons to create a chamber therebetween, stimulating a flow of blood cells by inflating the third balloon until the abrasive outer surface abrades tissue, and delivering the agent to the chamber. A balloon catheter system is also provided including a balloon having a wall with an abrasive outer surface for abrading tissue, a catheter having a first lumen for supplying fluid to the balloon to inflate the balloon such that the abrasive surface stimulates a flow of blood cells, and a second lumen for supplying an agent to tissue.

34 Claims, 10 Drawing Sheets

(56) References Cited

U.S. PATENT DOCUMENTS

| | | |
|---|---|---|
| 5,304,121 A | 4/1994 | Sahatjian |
| 5,336,234 A | 8/1994 | Vigil et al. |
| 5,397,307 A | 3/1995 | Goodin |
| 5,423,745 A | 6/1995 | Todd et al. |
| 5,545,133 A | 8/1996 | Burns et al. |
| 5,599,307 A | 2/1997 | Bacher et al. |
| 5,611,775 A | 3/1997 | Machold et al. |
| 5,647,847 A | 7/1997 | Lafontaine et al. |
| 5,674,192 A | 10/1997 | Sahatjian et al. |
| 5,707,352 A | 1/1998 | Sekins et al. |
| 5,728,064 A | 3/1998 | Burns et al. |
| 5,785,685 A | 7/1998 | Kugler et al. |
| 5,833,644 A | 11/1998 | Zadno-Azizi et al. |
| 5,868,708 A * | 2/1999 | Hart et al. ............... 604/104 |
| 5,873,852 A | 2/1999 | Vigil et al. |
| 5,932,248 A | 8/1999 | Chen et al. |
| 6,048,332 A | 4/2000 | Duffy et al. |
| 6,129,705 A | 10/2000 | Grantz |
| 6,190,354 B1 | 2/2001 | Sell et al. |
| 6,245,008 B1 | 6/2001 | Leschinsky et al. |
| 6,248,092 B1 | 6/2001 | Miraki et al. |
| 6,485,500 B1 | 11/2002 | Kokish et al. |
| 6,544,221 B1 | 4/2003 | Kokish et al. |
| 6,616,597 B2 | 9/2003 | Schock et al. |
| 6,623,452 B2 | 9/2003 | Chien et al. |
| 6,685,648 B2 | 2/2004 | Flaherty et al. |
| 6,733,459 B1 | 5/2004 | Atsumi |
| 7,014,652 B2 | 3/2006 | Cioanta et al. |
| 7,025,718 B2 | 4/2006 | Williams |
| 7,047,058 B1 | 5/2006 | Dvorsky et al. |
| 7,462,165 B2 | 12/2008 | Ding et al. |
| 7,569,032 B2 | 8/2009 | Naimark et al. |
| 7,611,484 B2 * | 11/2009 | Wellman et al. ......... 604/103.08 |
| 7,658,966 B2 | 2/2010 | Kokish |
| 7,727,226 B2 | 6/2010 | Chang et al. |
| 8,052,668 B2 * | 11/2011 | Sih ............................ 604/509 |
| 2002/0010418 A1 | 1/2002 | Lary et al. |
| 2003/0114791 A1 * | 6/2003 | Rosenthal et al. ......... 604/96.01 |
| 2004/0059290 A1 | 3/2004 | Palasis |
| 2004/0215140 A1 | 10/2004 | Forman |
| 2005/0015049 A1 | 1/2005 | Rioux et al. |
| 2006/0135984 A1 * | 6/2006 | Kramer et al. ................ 606/192 |
| 2006/0189930 A1 * | 8/2006 | Lary et al. ................ 604/101.01 |
| 2007/0027075 A1 * | 2/2007 | Smithrud ........................ 514/12 |
| 2007/0060942 A2 * | 3/2007 | Zadno-Azizi ................ 606/194 |
| 2007/0073264 A1 * | 3/2007 | Stedman et al. .............. 604/500 |
| 2008/0039791 A1 | 2/2008 | Abboud et al. |
| 2008/0051627 A1 | 2/2008 | Raju |
| 2008/0171985 A1 | 7/2008 | Karakoca |
| 2008/0208118 A1 * | 8/2008 | Goldman ................ 604/103.01 |
| 2008/0300571 A1 * | 12/2008 | LePivert ...................... 604/503 |
| 2009/0229374 A1 | 9/2009 | Carlisle et al. |
| 2010/0074895 A1 * | 3/2010 | Petricoin et al. ........... 424/133.1 |
| 2010/0113939 A1 | 5/2010 | Mashimo et al. |
| 2010/0121270 A1 | 5/2010 | Gunday et al. |
| 2010/0145398 A1 | 6/2010 | Li et al. |
| 2010/0280451 A1 | 11/2010 | Teeslink et al. |
| 2011/0082427 A1 * | 4/2011 | Golzarian et al. ............. 604/187 |
| 2011/0293629 A1 * | 12/2011 | Bastid et al. ................ 424/158.1 |

FOREIGN PATENT DOCUMENTS

| | | |
|---|---|---|
| WO | 9304727 A1 | 3/1993 |
| WO | 2006130326 A2 | 12/2006 |
| WO | 2009046206 A1 | 4/2009 |
| WO | 2009086269 A2 | 7/2009 |

OTHER PUBLICATIONS

International Search Report and Written Opinion of the International Searching Authority; PCT/US2010/034689; Jul. 15, 2010; 10 pages.

International Search Report & Written Opinion of the International Searching Authority; Application No. PCT/US2012/027197; Issued: Jun. 22, 2012; Mailing Date: Jul. 5, 2012; 9 pages.

European Search Report; Application No. EP 12 15 7640; Issued: May 20, 2012; Mailing Date: Jun. 8, 2012; 7 pages.

Altinoz, et al.; "Noscapine and Diltiazem Augment Taxol and Radiation-Induced S-Phase Arrest and Clonogenic Death of C6 Glioma in Vitro"; May 2006; Surgical Neurology; 65(5):478-84.

* cited by examiner

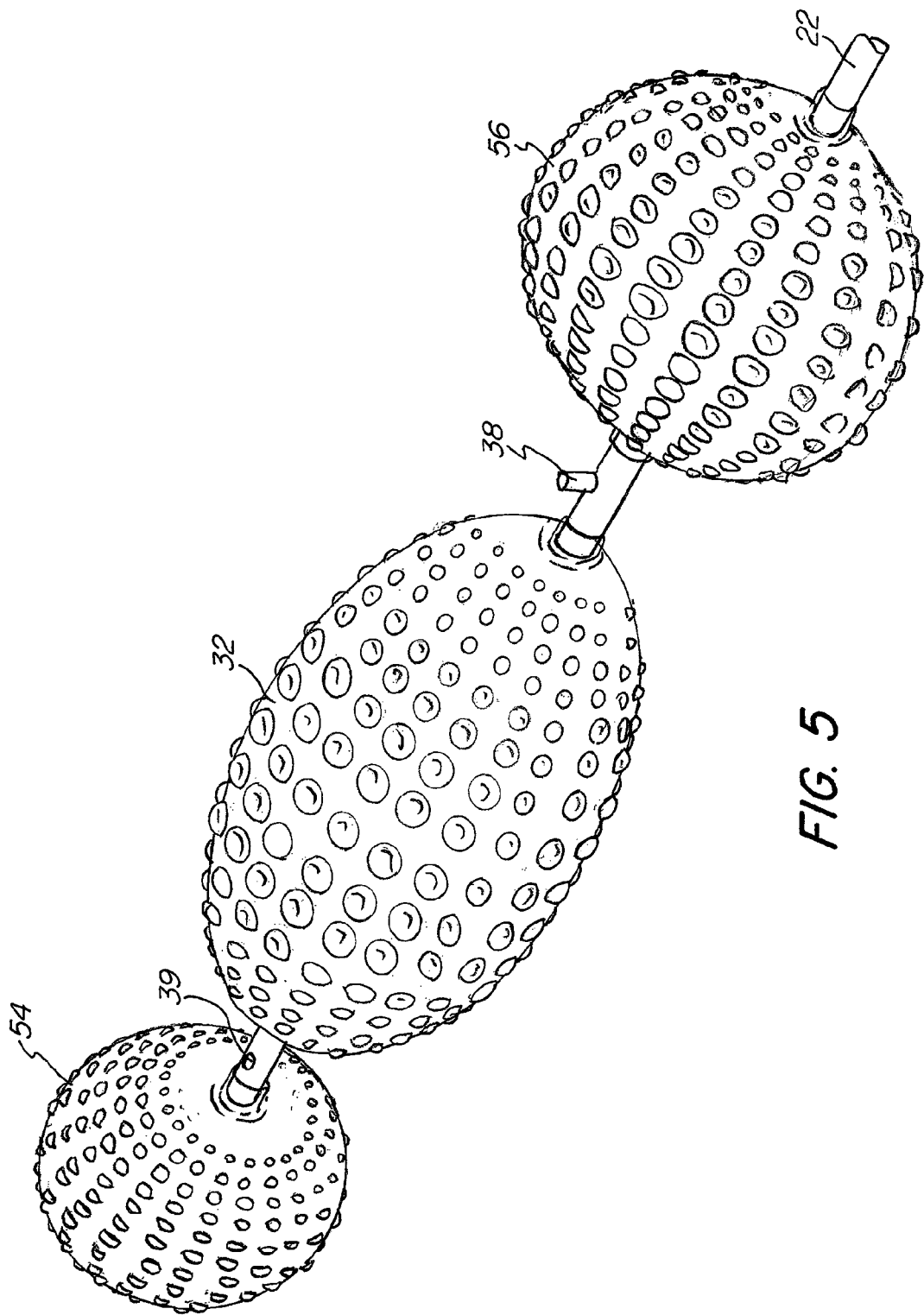

ABRADING BALLOON CATHETER FOR EXTRAVASATED DRUG DELIVERY

The present application is a continuation-in-part of U.S. patent application Ser. No. 12/269,495 filed on Nov. 12, 2008, now U.S. Pat. No. 8,226,601 the disclosure of which is incorporated by reference herein in its entirety.

FIELD OF THE INVENTION

The present invention relates to methods and systems for delivering therapeutic and diagnostic agents to specific cellular locations within and adjacent to bodily tissues and cavities. More specifically, the invention relates to a system and method of extravasated delivery of diagnostic and/or therapeutic agents to bodily tissues and cavities via a catheter that has a balloon with abrasive surface and that applies controlled pressure to the bodily tissues and cavities with a target biological material sandwiched between the balloon and the tissue, which stimulates flow of blood cells and facilitates extravasation of the agent into cellular membranes and structural walls of bodily cavities.

BACKGROUND OF THE INVENTION

In diagnosing and treating diseases of various body cavities and organs, it is necessary to deliver diagnostic and/or therapeutic agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic and diagnostic agents in general may not be delivered using these routes because they might be susceptible to enzymatic degradation or cannot be absorbed into the systemic circulation efficiently due to molecular size and charge issues, and thus, will not be fully therapeutically effective. For this reason, many such drugs have to be delivered by injection.

There are several known problems associated with the injection process. One of such problems is undesirable extravasation of the diagnostic or therapeutic agents into tissue, which is particularly prevalent with intravenously injected agents. Extravasation generally refers to leakage of fluids out of a container, and more specifically refers to leakage of intravenous drugs from a vein into surrounding tissues, resulting in an injury to the tissues. Once the intravenous extravasation has occurred, damage can continue for months and involve nerves, tendons and joints. If treatment is delayed, surgical debridement, skin grafting, and even amputation have been known to be the unfortunate consequences.

Occurrence of extravasation is possible with all intravenuous drugs, but it is a particularly significant problem with cytoxic drugs used for treatment of cancer (i.e. during chemotherapy).

Chemotherapy is the general term for any treatment involving the use of chemical agents to stop cancer cells from growing. Chemotherapy can eliminate cancer cells at sites great distances from the original cancer. As a result, chemotherapy is considered a systemic treatment. More than half of all people diagnosed with cancer receive chemotherapy. A chemotherapy regimen (a treatment plan and schedule) usually includes drugs to fight cancer plus drugs to help support completion of the cancer treatment.

Chemotherapy can be administered through a vein, injected into a body cavity, or delivered orally in the form of a pill, depending on which drug is used. Chemotherapy works by destroying cancer cells. Unfortunately, it cannot tell the difference between a cancer cell and some healthy cells. Thus, chemotherapy often eliminates not only the fast-growing cancer cells, but also other fast-growing cells in the body, including hair and blood cells. Some cancer cells grow slowly while others grow rapidly. As a result, different types of chemotherapy drugs target the growth patterns of specific types of cancer cells.

Each chemotherapy drug works differently and is effective at a specific time in a life cycle of the cell it targets. Brachytherapy, sometimes called seed implantation, is an outpatient procedure used in the treatment of different kinds of cancer. The radioactive "seeds" are carefully placed inside of the cancerous tissue and positioned in a manner that will attack the cancer most efficiently. The radioactive seeds are about the size of a grain of rice, and give off radiation that travels only a few millimeters to kill nearby cancer cells. There are two different kinds of brachytherapy: permanent, when the seeds remain inside the body, and temporary, when the seeds are inside of the body and are then removed. With permanent implants (e.g. prostate), the radioactivity of the seeds typically decays with time.

The other type of chemotherapy is when cytotoxic agents are delivered intravenously. Veins of people receiving chemotherapy are often fragile, mobile, and difficult to cannulate. Patients who receive chemotherapy at the same site as radiotherapy may experience a reactivation of skin toxicity known as a "recall" phenomenon. Patients who have had previous radiation therapy at the site of injection may develop severe local reactions from cytotoxic drugs. Cytotoxic drugs also have the potential to cause cutaneous abnormalities in areas that have been damaged previously by radiation, even in areas that are distant from the injection site. Patients who receive further chemotherapy in a different site may experience an exacerbation of tissue damage in the original site.

Furthermore, areas of previous surgery where the underlying tissue is likely to be fibrosed and toughened dramatically present an increased risk of extravasation. Radical mastectomy, axillary surgery or lymph node dissection may impair circulation in a particular limb. This reduces venous flow and may allow intravenous solutions to pool and leak around the site of cannulation.

Some chemotherapy drugs often never reach the tumors they are intended to treat because the blood vessels feeding the tumors are abnormal. A tumor's capillaries (small blood vessels that directly deliver oxygen and nutrients to cancer cells) can be irregularly shaped, being excessively thin in some areas and forming thick, snarly clumps in others. These malformations create a turbulent, uneven blood flow, so that too much blood goes to one region of the tumor, and too little to another. In addition, the capillary endothelial cells lining the inner surface of tumor capillaries, normally a smooth, tightly-packed sheet, have gaps between them, causing vessel leakiness.

The systemic and intravenous side effects of chemotherapy coupled with the limited effect of systemic administration due to abnormal characteristics of tumor blood vessels have given the scientific community pause, in searching for more direct, localized and biologic solutions. Accordingly, the oncology literature has become increasingly populated with articles espousing prospective benefits and positive outcomes of intra-tumoral chemotherapy. A direct administration of cytotoxic drugs such as Mytomycin, Mytomycin-C, Bleomycin, Fluorouracil, Mitoxantrone, Cisplatin, and Avastin in endobronchial intra-tumoral chemotherapy has been done experimentally via direct injection of the agent into the endobronchial tumor. In these cases, the tumor was reported to have died and been subsequently removed.

However, while some experimental uses of the localized delivery of cytotoxic drugs have been attempted, there has been little implementation of such drug delivery in practice, possibly due to numerous problems associated with such delivery. First, it is often necessary to deliver cytotoxic drugs to remote and not easily accessible blood vessels and other lumens within body organs, such as lungs. It is also important to be able to deliver defined doses of the cytotoxic substances because such substances are often very expensive or are capable of causing serious harm if delivered in excess. Moreover, the existing methods lack the ability to contain the cytotoxic agent and/or radiation therapy and mitigate collateral damage to non-affected anatomy and structures.

Several devices have been proposed for a targeted delivery of drugs to internal bodily cavities. For example, U.S. Pat. No. 6,048,332 to Duffy et al. discloses a drug delivery catheter that has a dimpled porous balloon mounted onto the distal end of the catheter. Each dimple has at least one aperture through which therapeutics agents are delivered to the tissue wall of a body lumen. U.S. Pat. No. 7,611,484 to Wellman et al. discloses a multi-balloon catheter designed for treatment of deceased blood vessels, and specifically lesions in the blood vessels. The catheter includes a pair of end balloons that, when inflated, isolate the deceased region of the blood vessel. The catheter further includes a middle balloon having an outer wall with a plurality of micro-needles that enable the therapeutic agents to be injected into the blood vessel wall.

While the above described catheter devices are useful for delivering the drugs to a specific target site, these systems are not particularly efficient at infusing the relevant biological material with the drug. Instead, the catheter may need to remain in place for an unnecessarily long period of time while the infusion of the drug into the biological material is allowed to take place. This is undesirable, especially in applications such as pulmonology, where the patient's respiratory passage has been somewhat restricted by the device. Further, this can result in some of the agent never being infused into the targeted material and instead remaining in the cavity and, after the balloon catheter is removed, subsequently migrating to other undesired portions of the body.

What is desired, therefore, is a balloon catheter system for delivering therapeutic and/or diagnostic agents to bodily tissues, tumors, and other biological materials that can locally deliver the agent to a specific target site. What is further desired is a balloon catheter system for delivering therapeutic and/or diagnostic agents that facilitates the infusion of the drug into surrounding bodily tissues, tumors, and other biological materials. What is also desired is a balloon catheter system for delivering therapeutic and/or diagnostic agents that can adjust for changing conditions during the process of delivering the drug.

SUMMARY OF THE INVENTION

Accordingly, it is an object of the present invention to provide an abrading balloon catheter system that can deliver therapeutic and/or diagnostic agents to bodily tissues, tumors, and other biological materials from within bodily cavities.

It is a further object of the present invention to provide an abrading balloon catheter system that can target specific areas for the delivery of therapeutic and/or diagnostic agents to bodily tissues, tumors, and other biological materials.

It is yet another object of the present invention to provide an abrading balloon catheter system that stimulates flow of blood cells and thereby facilitates infusion of therapeutic and/or diagnostic agents into surrounding bodily tissues, tumors, and other biological materials.

It is another object of the present invention to provide an abrading balloon catheter system for delivering therapeutic and/or diagnostic agents to bodily tissues, tumors, and other biological materials that permits the passage of bodily fluids through the system.

It is yet another object of the present invention to provide an abrading balloon catheter system for delivering therapeutic and/or diagnostic agents to bodily tissues, tumors, and other biological material that provides visualization from multiple possible views (i.e., distal, central, proximal, including from within an inflated balloon) within the bodily cavity.

In order to overcome the deficiencies of the prior art and to achieve at least some of the objects and advantages listed, the invention comprises a method of extravasated delivery of a therapeutic and/or diagnostic agent to tissue, including the steps of inserting a catheter into a bodily cavity, the catheter comprising a first balloon, a second balloon, and a third balloon positioned between the first and second balloons and having a wall with an abrasive outer surface, inflating the first and second balloons to create a chamber between the first balloon and the second balloon, stimulating a flow of blood cells by inflating the third balloon such that the abrasive outer surface abrades tissue in the bodily cavity, and delivering the therapeutic and/or diagnostic agent to the chamber.

In some embodiments, at least one additional balloon is positioned between the first and second balloons and has a wall with an abrasive outer surface.

In some embodiments, the step of stimulating the flow of blood cells further includes at least partially deflating the third balloon, and the method further comprises repeating the steps of inflating and at least partially deflating the third balloon.

In certain embodiments, the method further includes the step of increasing fluid pressure within the chamber by at least partially inflating the third balloon by supplying fluid thereto to facilitate extravasation of the agent into tissue in the bodily cavity.

In some advantageous embodiments, the method further includes the step of providing a vacuum to evacuate at least some of the agent from the chamber.

In certain embodiments, the method further includes the step of circulating the therapeutic agent within the chamber, wherein the agent enters the chamber through a first opening in the catheter positioned on one side of the third balloon and exits the chamber through a second opening in the catheter positioned on the other side of the third balloon.

The invention also comprises a method of extravasated delivery of a therapeutic and/or diagnostic agent to tissue, including the steps of inserting a catheter comprising at least one balloon having a wall with an abrasive outer surface into a bodily cavity, stimulating a flow of blood cells by inflating the at least one balloon by supplying fluid thereto via a first lumen of the catheter such that the abrasive surface abrades tissue in the bodily cavity, at least partially deflating the balloon, and delivering a therapeutic and/or diagnostic agent to tissue via a second lumen of the catheter.

In some advantageous embodiments, the method further comprises repeating the steps of inflating and at least partially deflating the at least one balloon.

In certain embodiments, the step of delivering the therapeutic and/or diagnostic agent to tissue comprises delivering the agent through at least one opening in the catheter in fluid communication with the second lumen.

In some embodiments, the wall of the at least one balloon has at least one opening in fluid communication with the second lumen and wherein the step of delivering the therapeutic and/or diagnostic agent to tissue comprises delivering the agent through the at least one opening and inflating the until it contacts the tissue.

In some cases, the step of inflating the at least one balloon comprises supplying fluid thereto with an electro-pneumatic pump.

In certain advantageous embodiments, the method further includes monitoring at least one vital sign of a patient.

In certain embodiments, the method further includes the step of using an imaging device disposed in the catheter to visualize tissue in the bodily cavity.

In some embodiments, the method further comprises the step of measuring at least one characteristic of tissue in the bodily cavity via at least one sensor.

In certain embodiments, the at least one balloon comprises a first balloon, the catheter further comprises a second balloon positioned distally of the first balloon and a third balloon positioned proximally of the first balloon, and the method further comprises the step of inflating the second and third balloons by supplying fluid thereto to create a chamber therebetween. In some of these embodiments, the first balloon and the second balloon each have a wall with a textured outer surface, and the step of inflating the first and second balloons further comprises contacting tissue in the bodily cavity with the textured surface to prevent slippage of the surface on the tissue.

In some embodiments, the agent is doxorubicin. In other embodiments, the agent is cisplatin, and the method further includes the step of supplying a second agent, the second agent being epinephrine. In further embodiments, the agent is 5-4 fluorouracil. In some embodiments, the agent is noscapine, and in some cases, the agent is diltiazem augment taxol. In other embodiments, the agent is crizotinib, gefitinib, or erlotinib hydrochloride. In some embodiments, the agent includes drug eluting microspheres, which in some cases, contain doxorubicin. In yet further embodiments, the agent is a combination of at least one therapeutic agent and at least one biomarker, and the method further includes the step of monitoring extravasation of the at least one therapeutic agent into tissue via the at least one biomarker. In some of these embodiments, the biomarker is a radio-opaque marker. In some cases, the abrasive surface of the balloon is radiopaque.

In certain embodiments, the step of delivering the therapeutic and/or diagnostic agent to tissue comprises coating at least part of the outer surface of the at least one balloon with the agent via the second lumen of the catheter and increasing the volumetric pressure exerted on the bodily cavity by supplying fluid to the at least one balloon to facilitate extravasation of the agent into the tissue.

The invention further comprises an abrading balloon catheter system for delivering a therapeutic and/or diagnostic agent to tissue, including at least one balloon having a wall comprising an outer surface for contacting tissue, wherein the outer surface comprises an abrasive surface for abrading the tissue, and a catheter having a first lumen through which fluid is supplied to the at least one balloon to inflate the balloon such that the abrasive surface stimulates a flow of blood cells in the tissue, and a second lumen for supplying a therapeutic and/or diagnostic agent to the tissue via at least one opening in the catheter.

In certain embodiments, the abrading balloon catheter system further includes a fluid source that supplies fluid to the first lumen of the catheter. In some of these embodiments, the fluid source comprises an electro-pneumatic pump. In certain of these embodiments, the pump supplies fluid to the at least one balloon in pulsed fashion to repeatedly deflate and inflate the balloon. In other embodiments, the fluid source further comprises a vacuum source that evacuates fluid from the at least one balloon.

In certain embodiments, the catheter includes a data device from which the pump is able to determine catheter characterization data.

In some embodiments, the at least one balloon comprises a first balloon, and the balloon catheter system further comprises a second balloon positioned distally of the first balloon and a third balloon positioned proximally of the first balloon, wherein the fluid source inflates the second and third balloons by supplying fluid thereto to create a chamber therebetween. In some of these embodiments, the second balloon and the third balloon each have a wall with a textured outer surface for preventing slippage of the outer surface on tissue.

In certain embodiments, the wall of the at least one balloon has at least one opening therein in fluid communication with the second lumen for supplying the therapeutic and/or diagnostic agent to tissue.

In some embodiments, the abrading balloon catheter further includes an imaging device disposed in the catheter for viewing tissue in a bodily cavity.

In certain advantageous embodiments, the abrasive surface of the at least one balloon comprises a mesh molded into the wall of the balloon. In other advantageous embodiment, the abrasive surface of the at least one balloon comprises surface structures encapsulated in the wall of the balloon.

In some cases, the abrading balloon catheter system further includes at least one imaging marker mounted adjacent the at least one balloon. In further embodiments, the fluid is a gas.

In certain embodiments, the catheter includes a distal tip with an opening therein and a third lumen in fluid communication with the opening in the distal tip for passing bodily fluids therethrough.

Other objects of the invention and its particular features and advantages will become more apparent from consideration of the following drawings and accompanying detailed description.

BRIEF DESCRIPTION OF THE DRAWINGS

FIG. 5 is an enlarged perspective view of the catheter system of FIG. 1 with a multi-balloon construct.

DETAILED DESCRIPTION OF THE INVENTION

Figure 1:
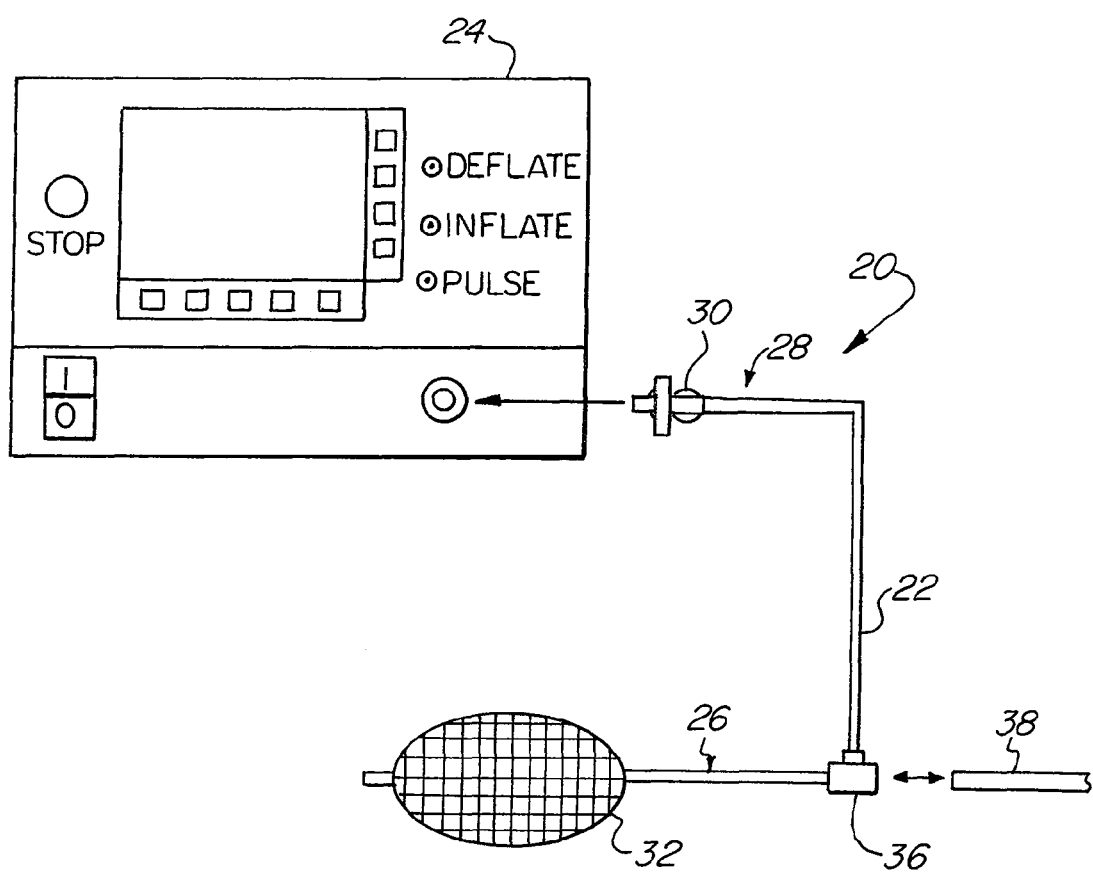
FIG. 1 is a schematic view of an abrading balloon catheter system for delivering therapeutic and/or diagnostic agents in accordance with the invention.

The basic components of one embodiment of an abrading balloon catheter system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, the abrading balloon catheter system (20) includes a catheter (22) and a fluid source (24). The catheter (22) may have any suitable diameter and length depending on a particular application, and may be flexible, rigid or semi rigid. The catheter (22) may be made with any commercially available material, such as polyethylene, that is flexible enough to allow the shaft to be safely inserted through the available opening of the working channel of an endoscope and a bodily cavity, it has a safety tip such that it will bend instead of puncturing the walls of the cavity, and at the same time is rigid enough such as it will maintain its shape as it is passed alongside and/or through the available opening of the bodily cavity. In an advantageous embodiment, the catheter (22) consists of a coil wire made of any suitable material, such as stainless steel, and a coating made of polyethylene. A distal end of the catheter (22) preferably includes a safety tip (not shown) that, when the catheter (22) is inserted into a bodily cavity, will bend instead of puncturing the walls of the cavity.

Any suitable fluid source may be used in accordance with the present invention. In the preferred embodiment shown in FIG. 1, the fluid source (24) is an electro-pneumatic pump having controls on the front thereof, from which a physician or assistant can control the system (as well as a remote control unit), such as that disclosed in U.S. Patent Application No. 2010/0121270 by Gunday et al., the specification of which is hereby incorporated by reference herein in its entirety. A proximal end (28) of the catheter (22) is connected to the pump (24) via a connection port (30). The port (30) is provided with any suitable connector, such as a luer connector, for connection to the pump. The pump (24) supplies a fluid, such as a gas, liquid, or mixture thereof, to the catheter (22). The pump (24) also includes a variety of capabilities for balloon identification, proper inflation/deflation of the balloons, and feedback measurements, many details of which are described in Gunday et al. In certain advantageous embodiments, the pump (24) further includes a vacuum source to evacuate fluid from the catheter (22).

In some embodiments, the catheter (22) includes a data device, which may, for example, be optical, RFID, flash memory, etc. As a result, the pump (24) is able to identify the type of catheter that is connected and read catheter characterization data (including pressure, volume, dimensions, etc.) included thereon, and then adjust its control accordingly based on user input.

The pump (24) also controls and regulates the pressure by monitoring and taking into account one or more vital signs of the patient, such as body temperature, heart rate, blood pressure, and respiratory rate. For example, in certain applications, it will be desirable to know the degree to which the lung is inflated at any given time in order to deliver a therapeutic and/or diagnostic agent at the right time. Similarly, in certain cases, it will be important to measure the systolic and diastolic blood pressure, and at appropriate times, apply a pressure that exceeds the systolic pressure in order to faciliate extravasation of an agent.

In an advantageous embodiment, the catheter (22) also includes a connection port (36) for insertion of an imaging device (38). The structure and operation of the imaging device is described in more detail below.

The abrading balloon catheter system (20) also includes an inflatable balloon (32) positioned at a distal end (26) of the catheter (22). The balloon (32) may be made of latex, Yulex, polyethylene, nylon or other suitable material, and may come in a variety of sizes and diameters, which allow the abrading balloon catheter system (20) to be used in bodily cavities of various diameters and dimensions, such as large and small bronchial branches, sinuses, and blood vessels, having different types of tumors and tissues to be treated.

The balloon (32) has a wall with an outer surface that comprises an abrasive surface intended to abrade bodily tissues, such as airway or vessel walls. The abrasion of the bodily tissues stimulates bleeding and instigates flow of white blood cells, i.e. leukocytes, out of the circulatory system towards the site of tissue damage. This process, together with the application of volumetric pressure or force to the abraded surface of the airway or the vessel wall to neutralize hemodynamic shear forces, perpetuates fluid extravasation processes and stimulates associated cellular absorption of the diagnostic and/or therapeutic agents into the adjacent tissues. The textured outer surface of the balloon (32) can also act as a gripping surface for attachment to bodily tissues, such as blood vessel walls, to anchor the balloon (32) at a target tissue site.

In one advantageous embodiment, the abrasive outer surface of the balloon (32) is formed by a fiber mesh affixed to the surface of the balloon during the molding process, which produces outwardly-facing protrusions that optimize the abrasion capability of the balloon (32). The fiber mesh may be made of lycra, polyurethane, nylon, nylon coated with other materials such as cotton, composite springs, or other appropriate material. In other advantageous embodiments, dimensional surface structures or inflatable sinuses that are encapsulated in the surface substrate of the balloon (32) may be used to produce the surface protrusions.

Figure 2A:
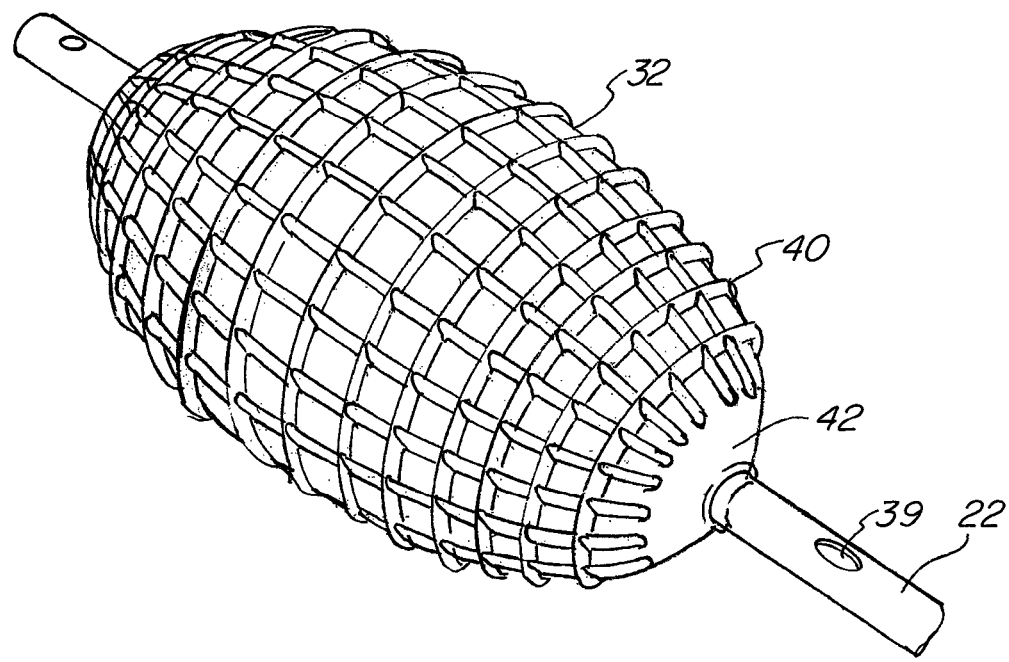
FIGS. 2A-2C are enlarged perspective views of an abrading balloon of the catheter system of FIG. 1.
Figure 2B:
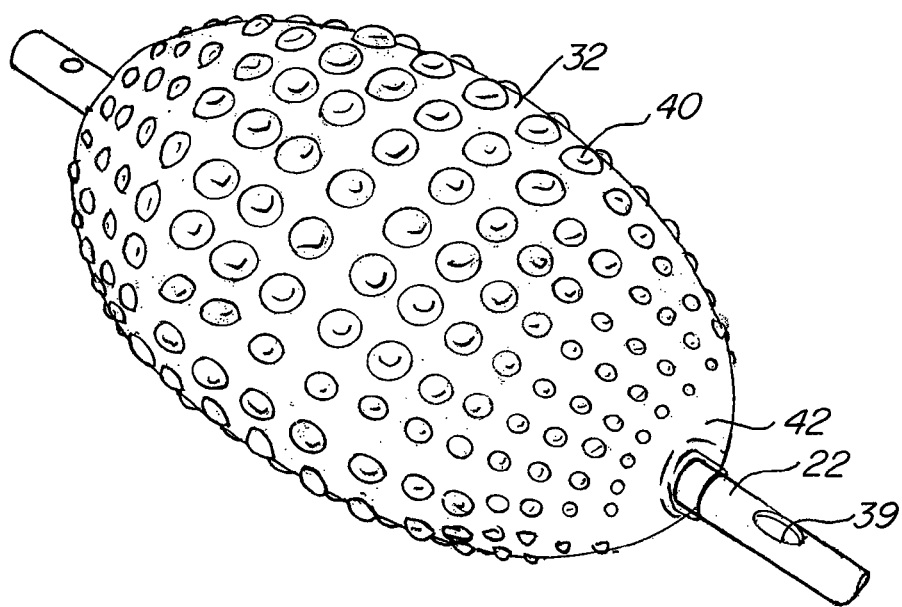
Figure 2C:
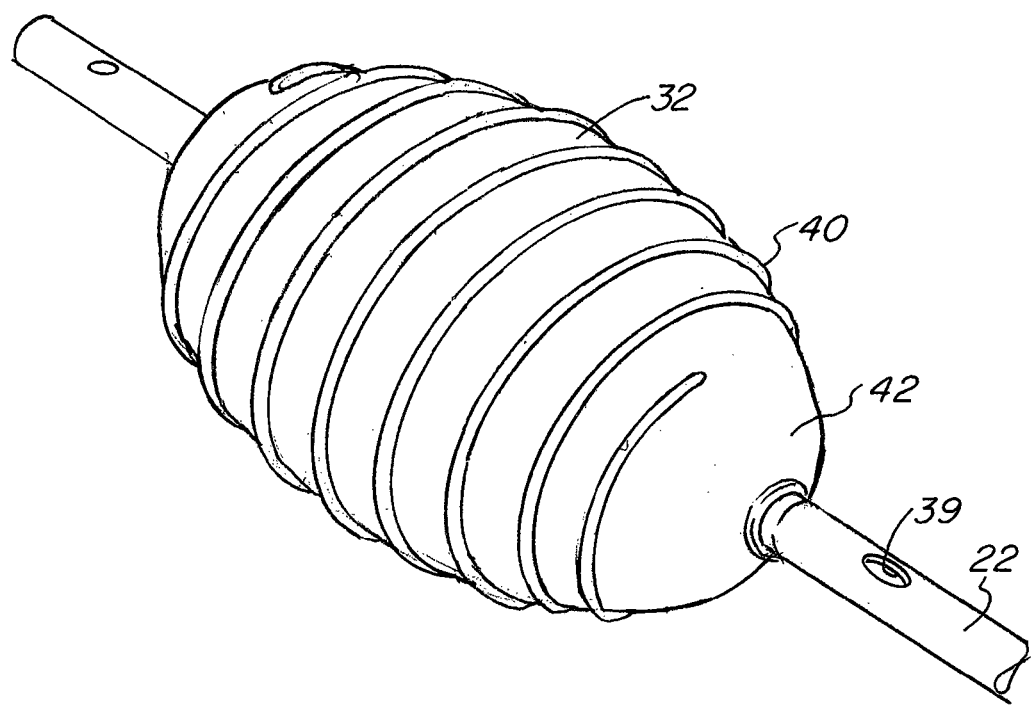

The protrusions forming the abrasive surface of the balloon (32) can have various shapes and configurations, depending on a particular application. For example, as shown in FIG. 2A, the outer surface (42) of the balloon (32) has outwardly extending protrusions (40) that form a lattice-like structure on the surface of the balloon (32). In another advantageous embodiment shown in FIG. 2B, the protrusions (40) are in a form of dimples that extend outwardly from the outer surface (42) of the balloon (32). In yet another advantageous embodiment illustrated in FIG. 2C, the protrusions (40) form a spiral-like pattern that extends circumferentially on the outer surface (42) of the balloon (32). It should be noted that any other shapes and configurations of the surface protrusions can be used in accordance with the present invention, including combinations of any of the aforementioned or other textures.

In certain advantageous embodiments, the balloon (32) includes imaging markers, such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloon (32) within a bodily cavity. Similarly, the balloon or balloon mesh may include a radiopaque material, such as a mesh made of yarn having radiopaque iron fibers.

Figure 3:
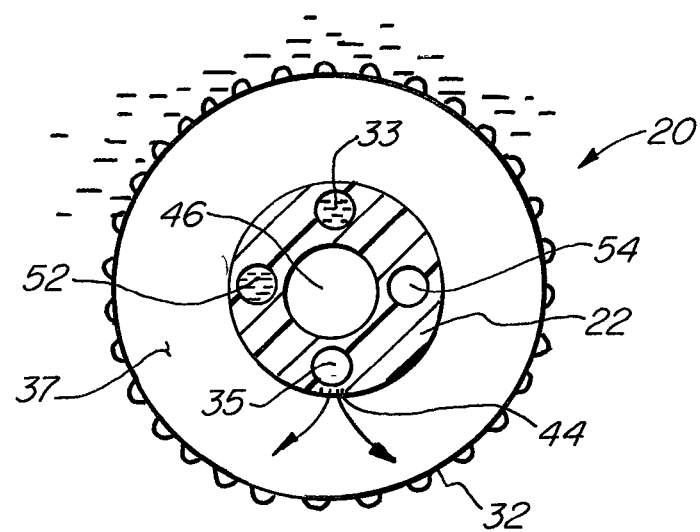
FIG. 3 is a cross-sectional view of the catheter system of FIG. 1.

The catheter (22) includes a first lumen (33) and a second lumen (35), as shown in FIG. 3. The first lumen (33) is in fluid communication with at least one opening (39) in the catheter (22) positioned on either side of the balloon (32). The catheter (22) can include multiple openings positioned on both sides of the balloon (32) or at any other suitable location along the catheter (22). The first lumen (33) is used to supply the therapeutic and/or diagnostic agent to tissue in the bodily cavity via the opening (39).

The balloon (32) at least partially encloses an inflation chamber (37), which is used to inflate the balloon. The second lumen (35) is in fluid communication with the inflation chamber (37) via at least one opening (44) in the catheter (22) positioned inside the inflation chamber (37). The second lumen (35) is used to supply fluid from the fluid source (24) to the inflation chamber (37) to inflate the balloon (32). It should be noted that in some embodiments, the wall of the balloon (32) has at least one opening therein, and the second lumen (35) is used to supply the therapeutic and/or diagnostic agent to the chamber (37), which is then delivered to tissue through the openings in the balloon wall.

The catheter (22) further includes a center lumen (46), which can be used to deliver any number of things, such as an imaging device, to assist insertion and positioning of the abrading balloon catheter system (20) within the bodily cavity and to carry out various medical procedures. It is understood that additional lumens, such as lumens (52) and (54) shown in FIG. 3, can be provided in the catheter (22) for introduction of various instruments and/or diagnostic/therapeutic agent (as further described below) that may be useful to carry out various diagnostic or therapeutic procedures. The center lumen (46) can also be used as a bypass channel to allow bodily fluids, such as air or blood, to flow through the balloon catheter, which is necessary in certain medical applications, e.g. pulmonology or cardiology. Though not all are shown, the referenced lumens each terminate and are accessible at the proximal end of the catheter (26). In certain cases, the lumen (46) is connected at the proximal end to a respiratory device.

Figure 4A:
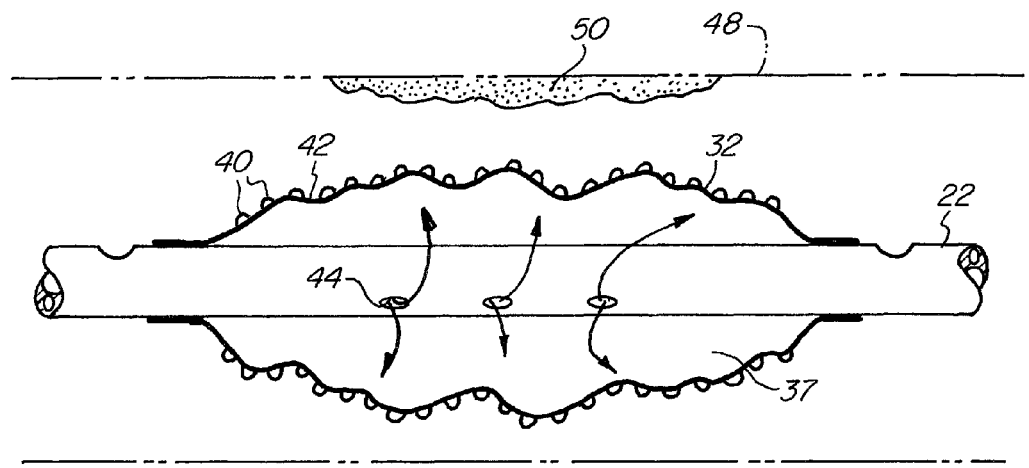
FIG. 4A is a partially exposed, isometric view of the catheter system of FIG. 1 positioned in a bodily cavity, showing the balloon in a deflated state.
Figure 4B:
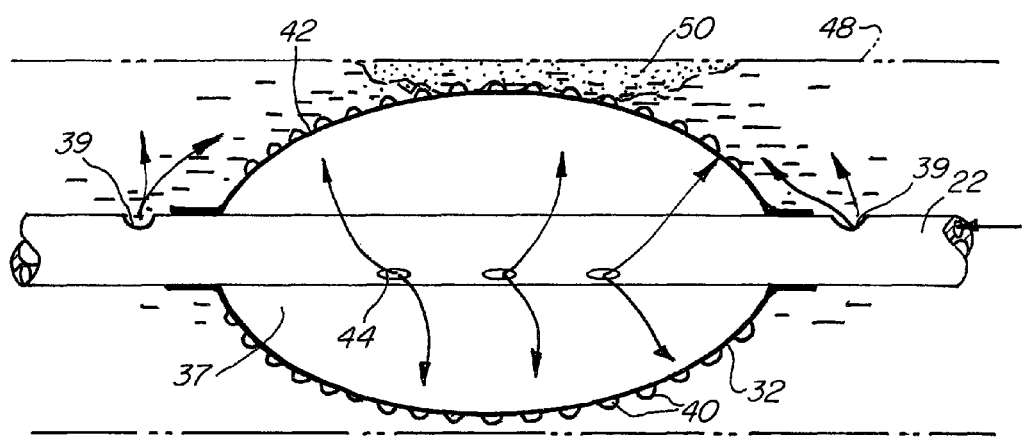
FIG. 4B is a partially exposed, isometric view of the catheter system of FIG. 1 positioned in a bodily cavity, showing the balloon in an inflated state.

FIGS. 4A and 4B illustrate a stepwise operation of the abrading balloon catheter system (20) in a bodily cavity. The catheter assembly (22) is first inserted into a bodily cavity (48) until the balloon (32) is in the vicinity of the target site, which in this case is a tumor (50). As shown in FIG. 4A, once the catheter (22) reaches the desired position in the bodily cavity (48), fluid is supplied to the inflation chamber (37) via the lumen (35) in the catheter (22) through the plurality of openings (44) to inflate the balloon (32). It should be noted that, although a plurality of openings (44) in the catheter (22) is illustrated in FIG. 4A, one opening is sufficient to supply fluid to inflate the balloon (32).

As the balloon (32) becomes inflated, the outer surface (42) of the balloon with the abrasive protrusions (40) comes into contact with surrounding tissue in the bodily cavity and begins to abrade the tissue, thereby prompting bleeding and stimulating a flow of leukocytes to the target tissue site. Then, the balloon (32) is at least partially deflated and a therapeutic and/or diagnostic agent is supplied via the lumen (33) and through the openings (39) in the catheter (22), such that the agent fills the space between the outer surface of the balloon (32) and the tumor tissue (50), as illustrated in FIG. 4B. The flow of blood cells caused by the abrasion of, and controlled pressure applied to, the tissue stimulates extravasation and associated cellular absorption of the diagnostic and/or therapeutic agent into the tissue.

In certain embodiments, the therapeutic and/or diagnostic agent is first delivered via the openings (39) to the space between the balloon (32) and the target tissue, such that the agent coats the outer surface (40) of the balloon (32). Then, the balloon (32) is inflated such that the abrasive surface and applied pressure of the balloon (32) abrades the tissue and stimulates the flow of blood cells, which in turn facilitates absorption of the agent into the tumor tissue (50). When the balloon (32) is fully inflated, the wall of the balloon is pressed against the tumor tissue (50), which further facilitates the absorption of the therapeutic and/or diagnostic agent into the tissue. Additionally, the inflation of the balloon (32) can assist in anchoring the balloon within the bodily cavity during the drug delivery process.

In some advantageous embodiments, the steps of inflating and at least partially deflating the balloon (32) are repeated by supplying fluid to the balloon (32) from the pump (24) in pulsed fashion. The repeated inflation and deflation of the balloon (32) causes enhanced abrasion of the tissue with the abrasive surface (40) of the balloon. Additionally, the repeated inflation and deflation of the balloon (32) causes a change in volumetric pressure exerted on a bodily lumen wall to neutralize hemodynamic shear forces and to stimulate extravasation of the therapeutic agent into tissue.

In additional advantageous embodiments, the therapeutic and/or diagnostic agent can also be supplied through at least one opening in the wall of the balloon (32). The balloon (32) is inflated such that the wall of the balloon (32) presses against the tumor tissue (50), and then the agent is delivered through the openings into the tissue. This way, the agent can be delivered to a more precisely targeted area of the tissue.

Any of various agents useful in therapeutic application can be delivered in the above described manner. For example, the agent may comprise one or more chemical or biological drugs with useful pharmacological properties, as well as any other medicaments or other substances with medicinal or other therapeutic uses. Such agents may be synthetic or natural, so long as they have an advantageous therapeutic effect that can obtained by delivering the agent to a target site. In certain embodiments, agents particularly useful for chemotherapies, radiation therapies, or immunotherapies are delivered as described above.

In some advantageous embodiments, a cytotoxic substance or other agent useful for chemotherapy is delivered to a target site via the abrading balloon catheter system of the present invention. For example, in some cases, the catheter system is used to deliver a chemical agent that affects cell division or DNA synthesis. Such agents include, for example, alkylating antineoplastic agents, such as cisplatin, carboplatin, oxaliplatin, mechlorethamine, carmustine, cyclophosphamide, chlorambucil, ifosfamide, busulfan, treosulfan, melphalan hydrochloride, thiotepa, and dacarbazine; anti-metabolites, such as azathioprine, mercaptopurine, thioguanine, fludarabine, pentostatin, cladribine, fluorouracil, floxuridine, cytosine arabinoside, gemcitabine, methotrexate, pemetrexed, and raltitrexed; anthracenedione antineoplastic agents, such as mitoxantrone; anthracyclines, such dactinomycin, daunorubicin, doxorubicin, epirubicin, idarubicin, valrubicin, aclarubicin, and bleomycin; plant alkaloids and terpenoids, such as noscapine, vincristine, vinblastine, vinorelbine, vindesine, podophyllotoxin, paclitaxel, and docetaxel; topoisomerase inhibitors, such as irinotecan, topotecan, amsacrine, etoposide, etoposide phosphate, and teniposide; and other agents with similar mechanisms of action, such as mitomycin C.

Other such agents include those that target molecular abnormalities, including tyrosine kinase inhibitors, such as crizotinib, gefitinib, erlotinib hydrochloride, imatinib, and imatinib mesilate. Still other such agents include those that modulate tumor cell behavior without actually attacking the cells, such as may be employed for hormone treatments. Indeed, any drug known to be efficacious in treating cancerous cells, such as streptozotocin or diltiazem augment taxol, may be employed.

In certain advantageous embodiments, a biological response modifier or other biological agent useful for immunotherapy is delivered to a target site via the abrading balloon catheter system. Such agents, which are often cytokines, may be a recombinant, synthetic, or natural preparation. These biological agents may include, for example, interferons, such as alpha-interferons and beta-interferons; interleukins, such as aldesleukin; colony-stimulating factors, such as filgrastim, sargramostim, epoetin, and oprelvekin; monoclonal antibodies, such as edrecolomab, rituximab, trastuzemab, gemtuzumab, alemtuzumab, nimotuzumab, cetuximab, bevacizumab, ibritumomab, panitumumab, and tositumomab; cancer vaccines; gene therapies; and non-specific immunomodulating agents. Any biologic known to useful for immunotherapies, such as asparaginase, may be employed.

In some advantageous embodiments, the therapeutic agent is delivered in drug eluting microspheres, which can be used both to cause the embolization of blood vessels that supply undesirable tissues and to retain the drug in a localized area for a sustained period of time. For example, drug-eluting microspheres can be used to deliver a chemotherapeutic drug, such as doxorubicin, to a tumor. When the microspheres reach the target site, they will block vessels supplying the tumor, and this suppression of blood flow will lead to ischemia. Over time, the microspheres break down, and the drug will be absorbed by the tissue. As a result, not only is a localized sustained release of the drug achieved, but the ischemia will also increase the effect of the drug on the tumor.

The above described delivery of therapeutic agents is also useful for radiation therapies, in which high-energy radiation is used to kill cancer cells and shrink tumors. One method of such therapy places radioactive material in the body near the cancer cells. Thus, in certain advantageous embodiments, a radioactive substance, such as a radiolabeled monoclonal antibody, is supplied via the abrading balloon catheter and extravasated into nearby tissue as described below.

Various agents may also be employed to assist in making diagnostic observations or monitoring procedures. For example, in some advantageous embodiments, the above described system may be used to deliver a contrast agent that allows or improves visualization via one or imaging modalities, which can be used to image the extravasation of the agent into the surrounding tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one can visually identify the extravasation depths and/or discern the requisite volumetric pressure, force, temperature, frequency and/or time to achieve efficacious delivery of the therapeutic agent to the desired depth of penetration at the intended treatment site.

The abrading balloon catheter system of the present invention can also be used to supply various media, e.g. light based therapies, radiofrequency wave forms, thermal energies and temperatures, and pressured air, to modulate cellular response sufficient to achieve tumoral destruction and to alter cellular membrane integrity to facilitate extravasation of medicinal and/or diagnostic agents into bodily tissues.

In certain embodiments, the catheter (22) has multiple lumens to supply therapeutic agents to the target tissue, which allows for delivery of multiple agents separately, as may be desired when using two different pharmaceuticals that should not be mixed until just before being extravasated into bodily tissue. For example, as shown in FIG. 3, the catheter (22) can include two delivery lumens (33) and (52), each supplying a different agent via a separate opening in the catheter. Likewise, one may need to deliver one medicinal agent at the beginning of the procedure, and another medicinal agent at a later time during the procedure. Furthermore, one may wish to deliver a second agent at a slightly different location than the first agent, which can be accomplished by providing two separate openings in the catheter (22), such as, for example, one at the distal end of the balloon (32) and the other at the proximal end of the balloon (32), and delivering each agent to tissue adjacent to each of the openings.

In an advantageous embodiment, an imaging device disposed in one of the lumens of the catheter (22) can be used to help position the balloon (32) at the proper location. For example, the lumen (33) that delivers the therapeutic and/or diagnostic agent may be large enough to also accommodate the imaging device, such that the imaging device can exit one of the openings (39), through which the agent is delivered to tissue. Preferably, the imaging device extends out of the opening (39) in the catheter (22) positioned at the distal end of the balloon (32), such that the tissue in front of the catheter can be viewed by the imaging device during the insertion of the abrading balloon catheter (20) into a bodily cavity. In this embodiment, the wall of the outer balloon (32) is transparent such that the imaging device can view the surrounding tissue through the wall.

In other embodiments, the wall of the balloon (32) is transparent, and the imaging device is introduced via the lumen (35), through which fluid is supplied to the inflation chamber (37) to inflate the balloon (32), and is extended out of one of the openings (44) in order to view the surrounding area through the transparent wall of the balloon. This has the added advantage that the lenses of the image device will not be contaminated and will not need to be cleaned. Alternatively, an additional lumen can be provided in the catheter (22) to accommodate the imaging device, such as the center lumen (46), and this lumen can connect to an opening leading to the inside of the balloon (32) or to one of the openings (39) in the catheter outside the balloon (32).

In some advantageous embodiments, the distal end of the catheter (22) includes a transparent membrane made out of any suitable material. The imaging device is extended through one of the lumens of the catheter to the membrane, which allows for visualization of the area ahead of the catheter (22). In this way, the physician can be provided with illuminated light and direct visual feedback of the area ahead of the balloon catheter, along the sides of the balloons, and/or behind the balloons.

In other advantageous embodiments, the lumen of the catheter (22), in which the imaging device is disposed, has an opening at a distal end, and the imaging device is extended out of the opening to visualize tissue in front of the abrading balloon catheter system (20). In this embodiment, the catheter (22) can also be provided with a cleaning device at the distal tip for cleaning the imaging device. The cleaning device is made with any suitable type of material, such as textile bundle, and is affixed to an inner surface of the catheter (22) adjacent to the opening at the distal end. The imaging device is cleaned by moving it back and forth through the textile bundle, thus wiping a lens of the imaging device.

The imaging device can be any device suitable for viewing the target area, such as a coherent fiber bundle or appropriate optical element and lens assembly in conjunction with an imaging sensor (e.g., CMOS, CCD), having a sufficiently small outer diameters, such as, for example, 0.75 mm-1.5 mm. In some cases, the imaging device has a pre-shaped distal tip that enables it to easily extend through one of the aforementioned openings. The distal tip of the imaging device is preferably flexible such that it can be translated linearly or rotationally thereby allowing for 360° visualization of the surrounding area.

FIG. 5 illustrates another embodiment of the abrading balloon catheter system of the present invention. In this embodiment, the catheter further includes a proximal balloon (56) positioned proximally of the balloon (32) and a distal balloon (54) positioned distally of the balloon (32). The catheter (22) includes two additional lumens, one in fluid communication with the proximal balloon (56) and the other in fluid communication with the distal balloon (54). It should be noted that a single lumen can be provided instead of the two lumens to supply fluid to both proximal and distal balloons. It should be noted that different manufacturing methods can be employed to create the illustrated dimples in order to make the dimples expand to different degrees.

The catheter (22) includes two openings (39), one positioned between the distal balloon (54) and the balloon (32) and the other positioned between the proximal balloon (56) and the balloon (32). The openings (39) are used to supply the therapeutic and/or diagnostic agent via the lumen (33). It is understood, however, that one opening is sufficient to supply the agent. Additionally, a plurality of openings can be provided along the catheter to supply the agent to different locations in the bodily cavity. In a preferred embodiment, the openings (39) are used to accommodate the imaging device (38) that extends out of the opening (39) such that the surrounding tissue can be viewed by the imaging device (38) during the insertion of the abrading balloon catheter (20) into the bodily cavity.

As shown in FIG. 5, the proximal and distal balloons (54, 56) are provided with a textured surface that assists in gripping of the balloons to the surrounding tissue upon inflation to facilitate secure positioning of the balloons in the bodily cavity. The walls of the proximal and distal balloons (54, 56) can be made transparent to enable visualization via the imaging device disposed inside the balloons, as described above with respect to the balloon (32) above.

Figure 6A:
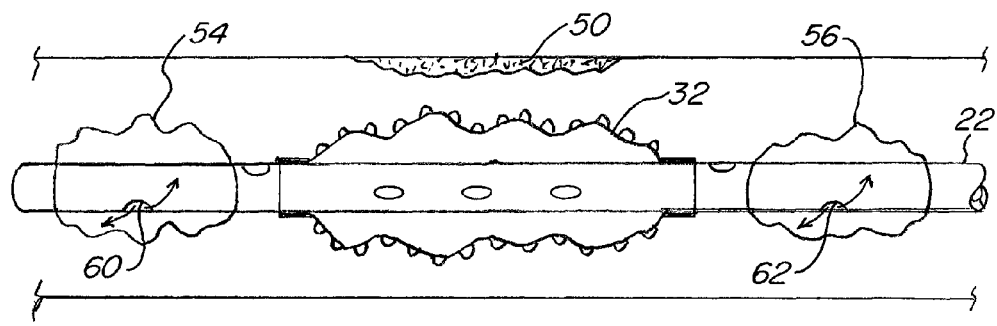
FIGS. 6A-6C are partially exposed, isometric views of the catheter system of FIG. 5 being operated in a bodily cavity.

Once the abrading balloon catheter (20) is introduced into a bodily cavity and positioned at a target site, the proximal balloon (56) and the distal balloon (54) are inflated by supplying fluid thereto by the pump (24) via at least one opening (60, 62) positioned inside each of the balloons (54, 56), as shown in FIG. 6A. The proximal and distal balloons (54, 56) are inflated simultaneously to create a chamber therebetween (58), into which the therapeutic and/or diagnostic agents are delivered through the openings (39) in the catheter (22). Alternatively, the distal balloon (54) is inflated first and is used as an anchor to secure the balloon catheter assembly at the target site, and then the proximal balloon (56) is inflated to create the chamber (58).

The chamber (58) functions to isolate the target treatment site from the surrounding tissue, which is particularly desirable during delivery of highly toxic chemotherapy agents to decrease exposure to such agents. Additionally, by creating the fluidly isolated chamber (58), it is possible to change volumetric pressure within the chamber to facilitate extravasation of the agent into target tissue. This can be achieved by repeatedly inflating and deflating the balloon (32) such that the fluid pressure in the chamber (58) is increased and decreased successively.

Figure 6B:
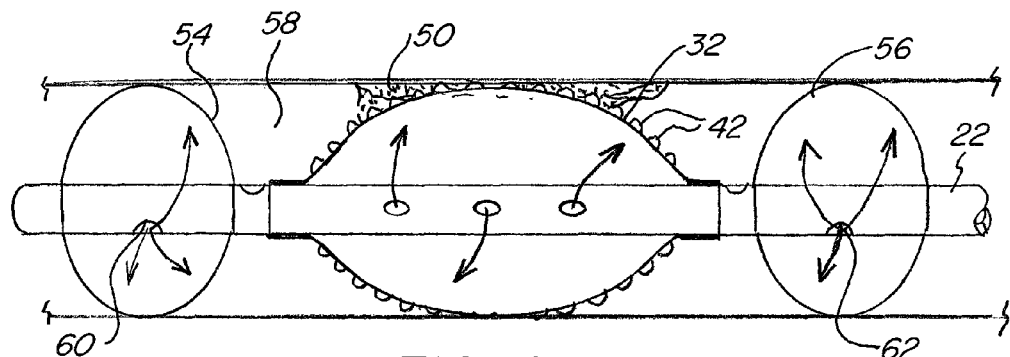

Once the proximal and distal balloons (54, 56) are inflated to create the chamber (58), the balloon (32) is inflated such that the abrasive outer surface (42) contacts the tumor tissue (50) and creates surface abrasions in the tissue, as illustrated in FIG. 6B. The surface abrasions act to create capillary blood flow and to instigate flow of white blood cells to the tissue, which facilitates absorption of the agent into the tissue. The balloon (32) can be sequentially pulsed to create further surface abrasions.

Figure 6C:
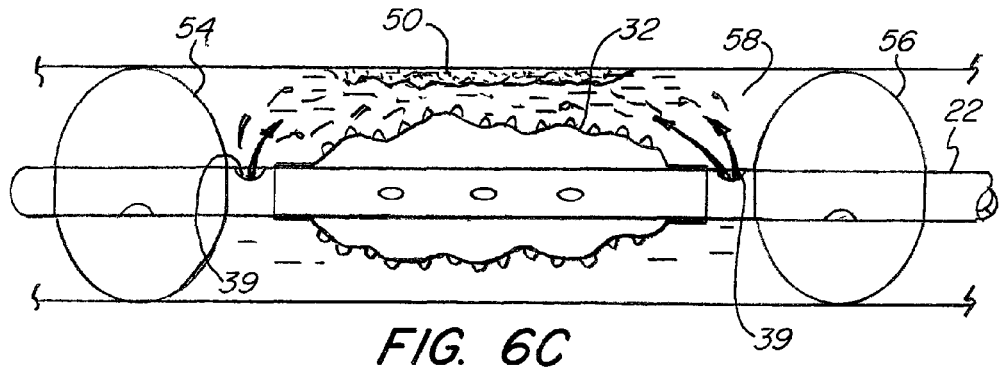

The therapeutic and/or diagnostic agent is then delivered into the chamber (58) via the openings (39) in the catheter (22), as shown in FIG. 6C. It should be noted that the agent can also be delivered through a plurality of openings provided in one or more of the balloons (32, 54, 56). As the agent fills the chamber (58), it coats the outer surface of the balloon (32). The balloon (32) is inflated, such that the outer surface of the balloon contacts the tumor tissue (50), and is kept that way for a desired period of time. The balloon (32) is then at least partially deflated, recoated with the agent, re-inflated and kept that way again. This sequential and/or constant expansion of the balloon (32) increases the volumetric pressure within the chamber (58), thereby neutralizing the hemodynamic shear forces, instigating leukocyte extravasation and initiating fluid extravasation through the vessel walls and into the adjacent tissues.

Once the agents have been delivered and extravasted into the tissue at the target site, any remaining agent can be evacuated from the chamber (58) via the same openings (39) and lumens through which they were supplied to the chamber (58) using suction. In certain advantageous embodiments, the fluid source (24) produces a negative pressure to vacuum out the agents. Alternatively, additional lumens and corresponding openings may be employed in the manner previously described to evacuate the agents through lumens different from those used to supply the agents to the chamber (58). Regardless, the various lumens and corresponding openings can be used to cyclically deliver and evacuate the agents and various other fluids instantly, sequentially, intermittently and/or continuously over designated time intervals.

In some embodiments, one of the lumens of the catheter (22) is used to supply an irrigation fluid. For example, when using both a therapeutic agent and a contrast agent, once the contrast agent has reached, and sufficiently saturated, the intended treatment site, any remaining contrast agent can be vacuumed out of the chamber (58). The chamber (58) can then be irrigated, lavaged, and suctioned to remove any residual agent.

Figure 7:
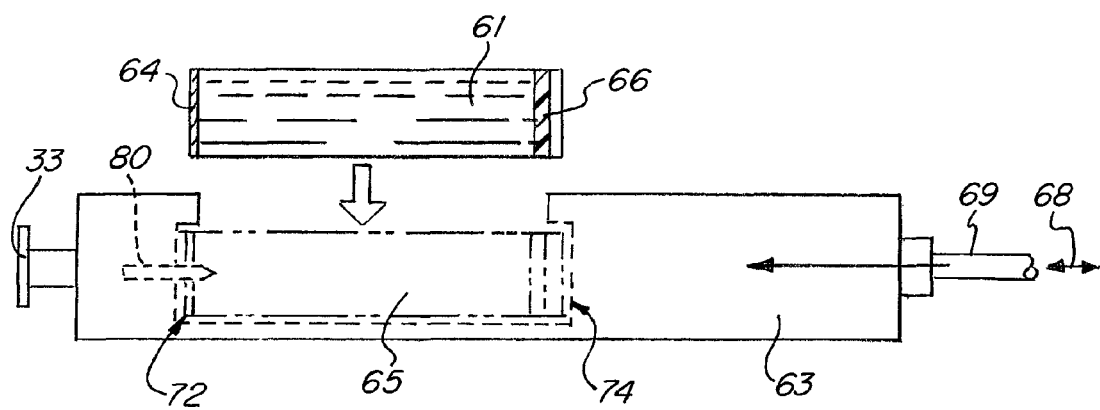
FIG. 7 is a schematic view of a drug delivery mechanism of the catheter system of FIG. 1.

The therapeutic and/or diagnostic agent can be delivered to the lumen (33) via any suitable mechanism. In one advantageous embodiment shown in FIG. 7, the therapeutic and/or diagnostic agent is contained in a drug capsule (61) adapted to be positioned into a delivery apparatus (63). The drug capsule (61) is prefilled with the agent and is sealed at a distal end by a piercable membrane (64) and at a proximal end by a slidable piston (66). The capsule (61) can be made out of any suitable material, and preferably is transparent such that the amount of the agent delivered can be monitored. The size of the drug capsule (61) and the amount of the agent it can hold can be variable depending on a particular application. For example, the capsule (61) can be filled with the amount of the agent to be delivered plus the amount needed to prime the drug delivery lumen (33) of the catheter (22).

The drug capsule (61) fits into a capsule compartment (65) of the delivery apparatus (63), which is connected to the delivery lumen (33) at a distal end (72) and is connected to a fluid source (68) at a proximal end (74) via a lumen (69). The fluid source (68) can be the same pump that is used to inflate the inner balloon or can be a separate pump. The distal end (72) of the capsule compartment has a needle (80) or any other suitable piercing device that functions to pierce the membrane (64) of the capsule (61). The proximal end (74) of the capsule compartment has an actuation mechanism adapted to actuate the piston (66) of the capsule (61). The capsule compartment (65) is preferably made out of transparent material such that the location of the piston can be determined and therefore the amount of the agent delivered can be observed and monitored.

The capsule (61) filled with the therapeutic and/or diagnostic agent is first positioned into the capsule compartment (65) of the delivery apparatus (63), such that the membrane (64) is pierced by the needle (80) located at the distal end (72) of the capsule compartment (65) to allow the agent to exit out towards the delivery lumen (33). Once the drug capsule (61) is securely positioned inside the capsule compartment (65), the actuation mechanism actuates the piston (66) such that it moves towards the distal end of the capsule (61), ejecting the therapeutic and/or diagnostic agent out of the capsule into the delivery lumen (33) of the catheter (22). If the agent to be delivered to tissue is in gaseous form, the delivery apparatus (63) can further include a valve (not shown) positioned at the distal end of the apparatus before the connection to the drug delivery lumen (33). The valve controls how much gaseous agent is delivered to the lumen (33), as well as the delivery time.

The actuator mechanism of the delivery apparatus (63) can be a pneumatic cylinder, into which fluid is supplied by the fluid source (68), wherein fluid pressure pushes the piston (66) forward, ejecting the agent out of the capsule (61). In other embodiments, the actuator mechanism can be an electrical motor, e.g. a stepper motor or a servo motor. The actuator mechanism (63) is connected to a controller that controls the quantity of the agent to be delivered and the delivery time period. The controller can be pre-programmed to deliver the exact quantity of drug over the exact amount of time, or it can be operated manually by the user during the procedure.

The piston (66) is preferably provided with a sensor, e.g. a magnetic sensor, optical or mechanical encoder, or any other suitable type of sensor, so that the position of the piston can be detected and communicated to the controller, which then determines how much drug has been delivered. A pressure transducer can also be provided at the distal end of the delivery apparatus (63) for measuring pressure in the drug delivery lumen (33) and reporting it to the controller that regulates the drug delivery rate and detects any problems that may arise. The controller also regulates and modulates the inflation and deflation of the inner balloon.

It should be noted that other embodiments of the drug delivery mechanism can be used without departing from the spirit of the present invention. The drug capsule prefilled with the agent to be delivered can be primed at any location along the catheter (22), such as, for example, adjacent to the balloon (32). The capsule can be disposed in the outer housing of the catheter or in any of the catheter lumens.

Figure 8:
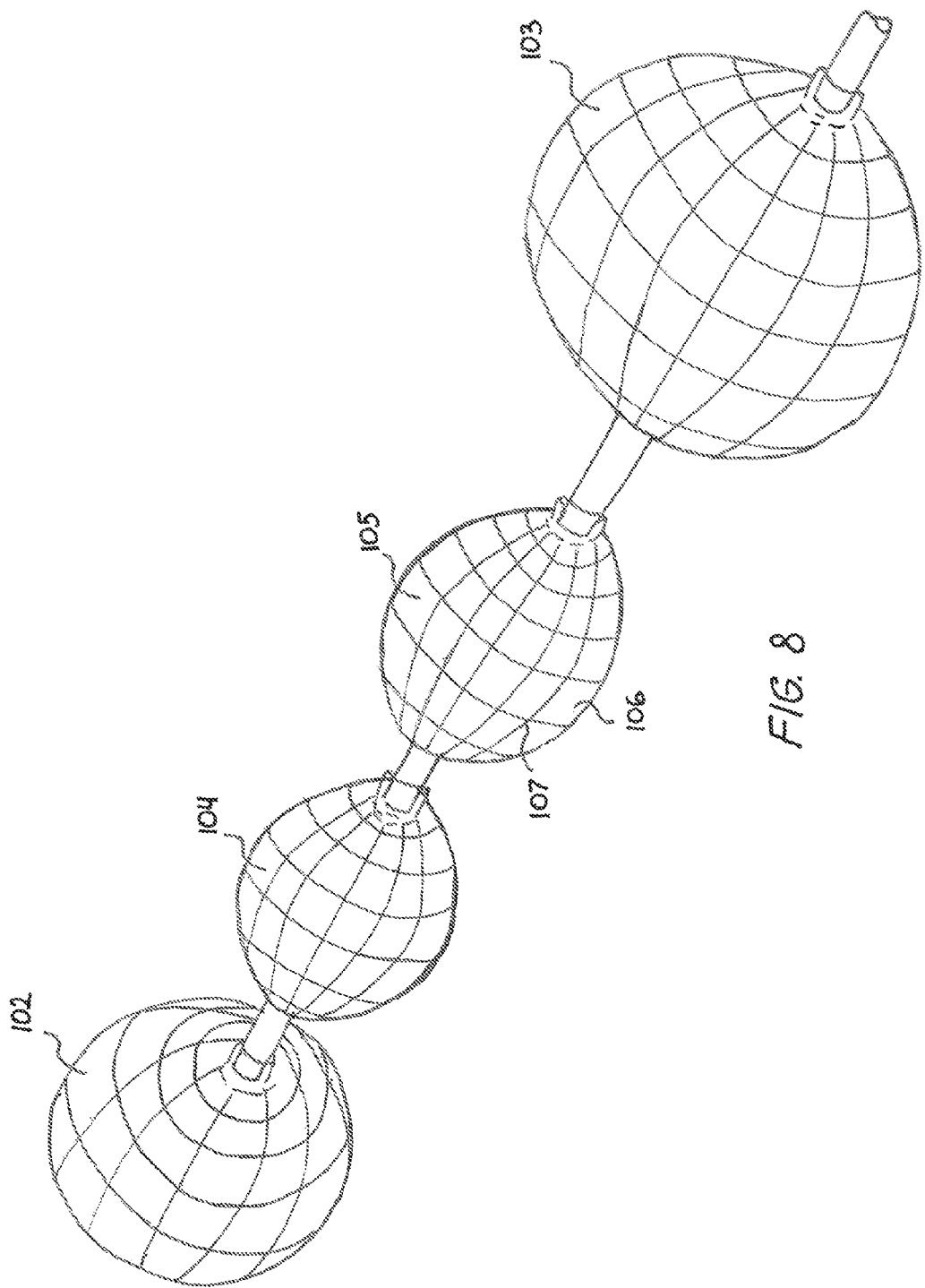
FIG. 8 is an enlarge perspective view of the catheter system of FIG. 1 with an alternative multi-balloon construct.

An additional embodiment of the abrading balloon catheter system of the present invention is illustrated in FIG. 8. In this embodiment, the catheter further includes a proximal balloon (102), a distal balloon (103), a first middle balloon (104) and a second middle balloon (105). Both of the middle balloons (104, 105) are positioned between the proximal and distal balloons (102, 103). In the embodiment shown in this figure, an outer wall (106) of the first and second balloons (104, 105) has abrasive surface (107) for abrading tissue in the bodily cavity once the middle balloons are inflated to stimulate a flow of blood cells.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of extravasated delivery of a therapeutic and/or diagnostic agent to tissue, comprising the steps of:
    inserting a catheter into a bodily cavity, said catheter comprising a first balloon; a second balloon; a third balloon positioned between the first and second balloons and having a wall with an abrasive outer surface; and at least one additional balloon positioned between the first and second balloons and having a wall with an abrasive outer surface;
    inflating the first and second balloons to create a chamber between the first balloon and the second balloon, wherein the boundaries of the chamber are defined by an inner surface of the cavity wall and the catheter;
    stimulating a flow of blood cells by inflating the third balloon such that the abrasive outer surface abrades tissue in the bodily cavity; and
    delivering the therapeutic and/or diagnostic agent to the chamber and external of the third balloon after stimulating the flow of blood cells.

2. The method of claim 1, wherein the step of stimulating the flow of blood cells further includes at least partially deflating the third balloon, and wherein the method further comprises repeating the steps of inflating and at least partially deflating the third balloon.

3. The method of claim 1, further comprising the step of monitoring at least one vital sign of a patient.

4. The method of claim 1, further comprising the step of increasing fluid pressure within the chamber by at least partially inflating the third balloon and supplying fluid thereto to facilitate extravasation of the agent into tissue in the bodily cavity.

5. The method of claim 1, further comprising the step of providing a vacuum to evacuate at least some of the agent from the chamber.

6. The method of claim 1, further comprising the step of circulating the therapeutic and/or diagnostic agent within the chamber, wherein the agent enters the chamber through a first opening in the catheter positioned on one side of the third balloon and exits the chamber through a second opening in the catheter positioned on the other side of the third balloon.

7. The method of claim 1, wherein the abrasive outer surface comprises a mesh affixed to the wall of the third balloon.

8. The method of claim 1, wherein the first balloon and the second balloon each have a wall with a textured outer surface and wherein the step of inflating the first and second balloons further comprises contacting tissue in the bodily cavity with the textured surface to prevent slippage of the surface on the tissue.

9. The method of claim 8, wherein the textured outer surface comprises a mesh affixed to the wall of the first and second balloons.

10. A method of extravasated delivery of a therapeutic and/or diagnostic agent to tissue, comprising the steps of:
inserting a catheter comprising at least one balloon having a wall with an abrasive outer surface into a bodily cavity;
stimulating a flow of blood cells by inflating said at least one balloon by supplying fluid thereto via a first lumen of the catheter such that the abrasive surface abrades tissue in the bodily cavity;
at least partially deflating said at least one balloon; and
delivering a therapeutic and/or diagnostic agent to tissue via a second lumen of the catheter, comprising coating at least part of the outer surface of the at least one balloon with the agent via the second lumen of the catheter and increasing a volumetric pressure exerted on the bodily cavity by supplying fluid to said at least one balloon to facilitate extravasation of the agent into the tissue.

11. The method of claim 10, wherein the abrasive outer surface comprises a mesh affixed to the wall of the at least one balloon.

12. The method of claim 10, further comprising repeating the steps of inflating and at least partially deflating said at least one balloon.

13. The method of claim 10, further comprising the step of monitoring at least one vital sign of a patient.

14. The method of claim 10, wherein the step of delivering the therapeutic and/or diagnostic agent to tissue comprises delivering the agent through at least one opening in the catheter in fluid communication with the second lumen.

15. The method of claim 10, wherein the wall of said at least one balloon has at least one opening in fluid communication with the second lumen and wherein the step of delivering the therapeutic and/or diagnostic agent to tissue comprises delivering the agent through said at least one opening and inflating said at least one balloon until it contacts the tissue.

16. The method of claim 10, wherein the step of inflating said at least one balloon comprises supplying fluid thereto with an electro-pneumatic pump.

17. The method of claim 10, further comprising the step of using an imaging device disposed in the catheter to visualize tissue in the bodily cavity.

18. The method of claim 10, further comprising the step of measuring at least one characteristic of tissue in the bodily cavity via at least one sensor.

19. The method of claim 10, wherein the agent is a combination of at least one therapeutic agent and at least one biomarker, and wherein the method further comprises the step of monitoring extravasation of the at least one therapeutic agent into tissue via the at least one biomarker.

20. The method of claim 19, wherein the biomarker is a radio-opaque marker.

21. The method of claim 10, wherein the abrasive surface of the balloon is radiopaque.

22. The method of claim 10, wherein said at least one balloon comprises a first balloon, wherein the catheter further comprises a second balloon positioned distally of the first balloon and a third balloon positioned proximally of the first balloon, and wherein the method further comprises the step of inflating the second and third balloons by supplying fluid thereto to create a chamber therebetween.

23. The method of claim 22, wherein the first balloon and the second balloon each have a wall with a textured outer surface and wherein the step of inflating the first and second balloons further comprises contacting tissue in the bodily cavity with the textured surface to prevent slippage of the surface on the tissue.

24. The method of claim 23, wherein the textured outer surface comprises a mesh affixed to the wall of the first and second balloons.

25. The method of claim 10, wherein the agent is doxorubicin.

26. The method of claim 10, wherein the agent is cisplatin, and wherein the method further comprises the step of supplying a second agent, said second agent being epinephrine.

27. The method of claim 10, wherein the agent is 5-4 fluorouracil.

28. The method of claim 10, wherein the agent is noscapine.

29. The method of claim 10, wherein the agent is diltiazem augment taxol.

30. The method of claim 10, wherein the agent is crizotinib.

31. The method of claim 10, wherein the agent is erlotinib hydrochloride.

32. The method of claim 10, wherein the agent is gefitinib.

33. The method of claim 10, wherein the agent comprises drug eluting microspheres.

34. The method of claim 33, wherein the drug eluting microspheres contain doxorubicin.

* * * * *

UNITED STATES PATENT AND TRADEMARK OFFICE
CERTIFICATE OF CORRECTION

PATENT NO. : 8,597,239 B2  
APPLICATION NO. : 13/037826  
DATED : December 3, 2013  
INVENTOR(S) : Lawrence J. Gerrans et al.

Page 1 of 1

It is certified that error appears in the above-identified patent and that said Letters Patent is hereby corrected as shown below:

On the Title page of the patent, Item (63) Related U.S. Application Data, please delete all the data with respect to the prior application.

In the Specification:

Column 1 of the patent, please delete the first paragraph, lines 4-7, with respect to the prior application.

Signed and Sealed this
Twenty-fifth Day of March, 2014

Michelle K. Lee
*Deputy Director of the United States Patent and Trademark Office*